US009192927B2

(12) United States Patent
Goossen et al.

(10) Patent No.: US 9,192,927 B2
(45) Date of Patent: Nov. 24, 2015

(54) METHOD FOR THE PREPARATION OF PALLADIUM(I) TRI-TERT-BUTYLPHOSPHINE BROMIDE DIMER AND PROCESS FOR ITS USE IN ISOMERIZATION REACTIONS

(75) Inventors: Lukas Goossen, Kaiserslautern (DE); Matthias Arndt, Kaiserslautern (DE); Patrizia Mamone, Gruenstadt (DE); Matthias Gruenberg, Schifferstadt (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 14/118,278

(22) PCT Filed: Jun. 25, 2012

(86) PCT No.: PCT/EP2012/062268
§ 371 (c)(1),
(2), (4) Date: Mar. 10, 2014

(87) PCT Pub. No.: WO2013/000874
PCT Pub. Date: Jan. 3, 2013

(65) Prior Publication Data
US 2014/0187803 A1 Jul. 3, 2014

(30) Foreign Application Priority Data
Jun. 29, 2011 (EP) .................... 11005326

(51) Int. Cl.
*B01J 31/24* (2006.01)
*C07D 307/68* (2006.01)
*C07C 67/293* (2006.01)

(52) U.S. Cl.
CPC ............. *B01J 31/24* (2013.01); *C07C 67/293* (2013.01); *C07D 307/68* (2013.01); *B01J 2231/52* (2013.01); *B01J 2531/0213* (2013.01); *B01J 2531/824* (2013.01)

(58) Field of Classification Search
CPC .................. B01J 31/24; B01J 2231/52; B01J 2531/0213; B01J 2531/824; C07C 67/293; C07D 307/68
USPC .............. 549/486; 560/113; 554/125; 556/23
See application file for complete search history.

(56) References Cited

FOREIGN PATENT DOCUMENTS

WO 2011012889 A1 2/2011

OTHER PUBLICATIONS

Barrios-Landeros, F.,"Autocatalytic Oxidative Addition of PhBr to Pd (P t Bu3) 2 via Pd (P t Bu3) 2 (H)(Br)." Journal of the American Chemical Society 130.18 (2008): 5842-5843.*

International Search Report for PCT/EP2012/062268; mailed Aug. 6, 2012.
Written Opinion for PCT/EP2012/062268; mailed Aug. 6, 2012.
Palladium-Catalyzed Amination of Aryl Bromides with Hindered N-Alkyl-Substituted Anilines Using a Palladium(I) Tri-tert-butylphosphine Bromide Dimer, M. Prashad, X.Y. Mak, Y. Liu, O. Repic, J. Org. Chem. 2003, 68, pp. 1163-1164.
Zinc-Mediated Palladium-Catalyzed Formation of Carbon-Sulfur Bonds, C.C. Eichmann, J.P. Stambuli, J. Org. Chem, 2009, 74, pgs. 4005-4008.
Scope and Mechanism of Palladium-Catalyzed Amination of Five-Membered Heterocyclic Halides, M.W. Hooper, M. Utsunomiya, J.F. Hartwig J. Org. Chem. 2003, 68, pgs. 2861-2873.
Two-Coordinate Palladium(0) Complexes, $Pd[PPh(t-Bu)_2]_2$ and $Pd[P(t-Bu)_3]_2$, Journal of the American Chemical Society, M. Matsumoto, H. Yoshioka, K. Nakatsu, T. Yoshida, S. Otsuka, J, Am. Chem. Soc. 1974, 96, pp. 3322-3324.
A Superior Precursor for Palladium(0)-Based Cross-Coupling and Other Catalytic Reactions, D.M. Norton, E.A. Mitchell, N.R. Botros, P.G. Jessop, M.C. Baird, J.Org. Chem. 2009, 74, pp. 6674-6680.
The First General Method for Palladium-Catalyzed Negishi Cross-Coupling of Aryl and Vinyl Chlorides: Use of Commercially Available $Pd(P((t-Bu)_3)_2$ as a Catalyst, C.Dai, G.C. Fu, J.Am. Chem. Soc. 2001, 123, pp. 2719-2724.
A Highly Efficient, Practical, and General Route for the Synthesis of $(R_3P)_2Pd(0)$: Structural Evidence on the Reduction Mechanism of Pd(II) to Pd(0), H. Li, G.A. Grasa, T.J. Colacot, Org. Lett. 2010, 12, pp. 3332-3335.
1,6-Diene Complexes of Palladium(0) and Platinum(0): Highly Reactive Sources for the Naked Metals and $[L-M^0]$ Fragments J.Krause, G. Cestaric, K-J. Haack, K. Seevogel, W. Storm, K-R. Porschke, J. Am. Chem, Soc. 1999, 121, pp. 9807-9823.
Reactions of Allylic Compounds Such as Allyl Alcohols, Allyl Ethers, and Allylamines Using $trans-Mo(N_2)_2(Ph_2PCH_2CH_2PPh_2)_2$, T. Tatsumi, K. Hashimoto, H. Tominaga, Y. Mizuta, K. Hata, M. Hidai, Y. Uchida, J. Organomet Chem. 1983, 252, pp. 105-112.
Chemistry of the Metal Carbonyls. Part XXXII. Isomer-isation of Allyl Compounds and the Dimerisation of Norbornadiene, P.W. Jolly, F.G.A. Stone, K. MacKenzie, J.Chem. Soc. 1965, pp. 6416-6420.
Iron Carbonyl Catalyzed Isomerization of unsaturated Ethers and Esters. The Effect of Carbomethoxy and Methoxy Groups on Olefin Equilibria [1], R.Damico, J.Org. Chem. 1968, 33, pp. 1550-1556.

(Continued)

*Primary Examiner* — Samantha Shterengarts
*Assistant Examiner* — John Mauro
(74) *Attorney, Agent, or Firm* — Smith, Gambrell & Russell, LLP

(57) ABSTRACT

The invention provides a new method for the preparation of the dimeric Pd(I) tri-tert.-butylphosphine bromide complex, characterized by the chemical formula $[Pd(\mu-Br)(P^tBu_3)]_2$. The method is based on a comproportionation reaction in which a Pd(II) compound ($=PdBr_2$) is reacted with a Pd(0) compound ($=Pd(P^tBu_3)_2$) in organic solvents to yield the $[Pd(\mu-Br)(P^tBu_3)]_2$ compound having the Pd atoms in the formal oxidation state +1. Unreacted $PdBr_2$ may be reused in the process. The method is straightforward and applicable for industrial scale production and provides high product yields. Further, a new process for the isomerization of allyl ethers of the general type $R_1-C(O)-O-CH(R_2)-C(R_3)=CH_2$ employing the compound $Pd(\mu-Br)(P^tBu_3)]_2$ as a catalyst is disclosed.

25 Claims, No Drawings

(56) References Cited

OTHER PUBLICATIONS

An Improved Method for Efficient Conversion of Unstaurated Alcohols, Ethers and Esters To Their Corresponding Aldehydes, Ketones, Enol Ethers and Enol Esters. N. Iranpoor, H. Irnanieh, Synth. Commun. 1989, 19, 2955-2961.

Selective Cleavage of Allyl Ethers under Mild Conditions by Transition Metal Regents, E.J. Corey, J.W. Suggs, J. Org. Chem. 1973, 38, p. 3224.

The Mechanism of Aqueous Ruthenium (II)-Catalyzed Olefin Isomerization, D.V. McGrath, R.H. Grubbs, Organometallics 1994, 13, pp. 224-235.

Isomerisation of Allyl Ethers Catalysed by the Cationic Iridium Complex [Ir(cyclo-octa-1,5-diene) $PMePh_2)_2]PF_6$ A Highly Stereoselective Route to trans-Propenly Ethers, D. Baudry, M. Ephritikihne, F. Felkin J. Chem. Soc., Chem. Commun. 1978, pp. 694-695.

Isomerisation of Allyl Phenyl Ethers and Allylphenols with Transition Metal Catalysts. P. Golborn. F. Scheinmann, J. Chem. Soc., Perkin. Trans. 1 1973, pp. 2870-2875.

Chemistry of Metal Hydrides. XIII. Insertion and Isomerization Reactions of Allylic Compounds with Cationic Platinum(II)-Hydrido Complexes, H.C. Clark, H. Kurosawa, Inorg. Chem. 1973, 12, pp. 357-362

Chemistry of Metal Hydrides. XV. Mechanism of Double-Bond Migration Induced by Platinum (II) Hydrides, H.C. Clark, H. Kurosawa. lnorg. Chem. 1973, 12, pp. 1566-1570.

Asymmetric isomerization of allylic compounds and the mechanism, K. Tani, Pure Appi, Chem, 1985, 57, pp. 1845-1854.

Palladium-Catalyzed Amination of Aryl and Heteroaryl Tosylates at Room Temperature, John F. Hartwig at al., J. Am. Chem Soc. 2008 pp. 13848-13849.

Structural Characterization and Simple Synthesis of {Pd[P(o-Tol)$_3$]$_2$}, Dimeric Palladium(II) Complexes Obtained by Oxidative Addition of Aryl Bromides, and Corresponding Monometallic Amine Complexes, John F. Hartwig et al., Organarnetallics 1995, 14, pp. 3030-3039.

Synthesis and structural characterization of $[Pd_2(\mu-Br)_2(PBu^t_3)_2]$, an example of a palladium(i)-palladium(I) dimer, M.P. Mingos et al. J. Chem. Soc., Dalton Trams. 1996, pp. 4313-4314.

Reactivity studios of $[Pd_2(\mu-X)2(PBu^t_3)2](X=Br, I)$ with CNR (R=2,6-dimethlphenyl), $H_2$ and alkynes, R. Vilar, D.M.P. Mingos et al., J. Organomet. Chem 2000, 600, pp. 198-205.

A Highly Active Palladium (I) Dimer for Pharmaceutical Applications $[Pd(\mu-Br)(^tBU_3P)]_2$ As A Practical Cross-Coupling Catalyst, T.J. Colacot, Platinum Metals Rev. 2009, 53, pp. 183-188.

Unparalleled Rates for the Activation of Aryl Chlorides and Bromides: Coupling with Amines and Boronic Acids in Minutes at Room Temperature, J.F. Hartwig at al., Angew. Chem. Int. Ed. 2002, 41, pp. 4746-4748.

Die Konstitution des Palladium (II)-bromids, K. Brodersen et al., Z. Anorg. Allgem. Chem. 1966, 348, pp. 162-167.

A Practical and Effective Ruthenium Trichloride-Based Protocol for the Regio-and Steroselective Catalytic Hydromidation of Terminal Alkynes, L.J. Gooβen et al., Adv. Synth, Catal. 2008, 350, pp. 2701-2707.

Dodecaoarbonyl triiron, an efficient catalyst for photochemical isomerization of unsaturated alcohols, ethers and ester to their corresponding carbonyl compounds, enol ethers and esters, Iranpoor et al., J. Organomet. Chem., 1992, 423 pp. 399-404.

The role of the functional group in double bond migration in allylic systems catalyzed by ruthenium hydride, complexes, Krompiec et al., J. Mol. Cat. A: Chemical, 2006, 253, pp. 132-146.

In Situ Generated Bulky Palladium Hydride Complexes as Catalysts for the Efficient lsomerization of Olefins. Selective Transformation of Terminal Alkenes to 2-Alkenes, Skrydstrup et al., J. Am. Chem. Soc. 2010, pp. 7998-8009.

Autocatalytic Oxidative Addition of PhBr to Pd (P$^t$Bu3)2 via Pd(PtBu$_3$0$_2$(H)(Br), J.F. Hartwig et al., J. Am. Chem Soc., 2008, 130, pp. 5842-5843.

Metal-catalyzed rearrangements of allylic esters, A. C. Oehlsclager et al., Can. J. Chem. 62, 1984, pp. 791-797.

\* cited by examiner

METHOD FOR THE PREPARATION OF PALLADIUM(I) TRI-TERT-BUTYLPHOSPHINE BROMIDE DIMER AND PROCESS FOR ITS USE IN ISOMERIZATION REACTIONS

The present invention is directed to the preparation of precious metal complexes, in particular to the preparation of a palladium phosphine complex.

The invention provides a new method for producing a dimeric Pd(I) bromophosphine complex, in particular the Pd(I) tri-tert-butylphosphine bromide dimer complex, characterized by the chemical formula $[Pd(\mu\text{-Br})(P^tBu_3)]_2$. The new method of the invention is economical and applicable for industrial scale production and provides high product yields. Further, a novel use of the dimeric Pd(I) bromophosphine complex $[Pd(\mu\text{-Br})(P^tBu_3)]_2$ as a catalyst is disclosed.

According to the present invention, the synthesis method of the Pd-complex uses educts which can be obtained easily and in high yields. The starting materials employed in the preparation method are easier to handle compared to the educts used in the literature. The preparation method according to the present invention is highly effective with regard to loss of valuable educts. In particular, an un-reacted educt can be isolated, recycled and used again.

The Pd-complex produced according to the method of the present invention shows improved catalytic activity in chemical reactions compared to respective catalysts made according to processes known from the art. As an example, higher yields in isomerization reactions of allyl esters can be achieved using the $[Pd(\mu\text{-Br})(P^tBu_3)]_2$-complex produced according to the method of the present invention.

Structure of and analytical data for the $[Pd(\mu\text{-Br})(P^tBu_3)]_2$-complex are well known from the prior art. X-ray crystal structure analysis of the $[Pd(\mu\text{-Br})(P^tBu_3)]_2$-complex suggests that the complex is a dimer with Pd—Pd bonding, stabilized by two bromine atoms via bridge formation (see for example M. P. Mingos et al. *J. Chem. Soc., Dalton Trans.* 1996, 4313-4314 and R. Vilar, D. M. P. Mingos et al., *J. Organomet. Chem.* 2000, 600, 198-205).

The Pd complex has the following structure (formula I):

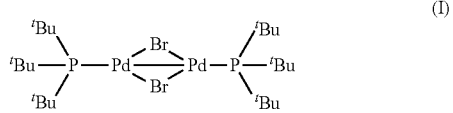

The compound is a dark green crystalline substance. Each Pd atom in the dimer has the oxidation state of +1. In chlorinated solvents the complex decomposes rapidly (ref to T. J. Colacot, *Platinum Metals Rev.* 2009, 53, 183-188).

Catalytic Activity of $[Pd(\mu\text{-Br})(P^tBu_3)]_2$

The dark green $[Pd(\mu\text{-Br})(P^tBu_3)]_2$-complex is able to form a catalytically active system in solution very rapidly. A highly reactive, single coordinated 12-electron species, $[Pd(P^tBu_3)]$, may be formed. The formation of this species is caused by in situ disproportionation or by direct reduction of the Pd-complex in presence of the substrate and a base.

From the prior art various reactions are known, which demonstrate the catalytic activity of the Pd-complex of formula I. The Pd-complex is predominantly used as a cross-coupling catalyst. In the scientific literature it is reported that 0.5 mol-% of the Pd-complex are able to catalyze Suzuki reactions as well as the coupling of C—N bonds in the presence of a simple hydroxide base (ref to J. F. Hartwig et al., *Angew. Chem. Int. Ed.* 2002, 41, 4746-4748). Sterically hindered, multiple substituted aryl bromides can react with boric acids at room temperature with high yields within just a few minutes. Using the present Pd catalyst, the reaction between aryl chlorides and various secondary amines occurred rapidly at room temperature. The Pd-complex is furthermore useful for C—S bonding and shows high catalytic activity in combination with zinc chloride catalyst.

PRIOR ART PREPARATION METHODS

In the prior art, different pathways for preparing di-μ-bromobis(tri-tert.-butyl-phosphine)-dipalladium(I) $[Pd(\mu\text{-Br})(P^tBu_3)]_2$ are discussed in detail by Mingos et al. and by Vilar et al. (references cited above). In a first pathway, the known synthesis method uses a Pd-"dba" complex as Pd source according to the following equation (I):

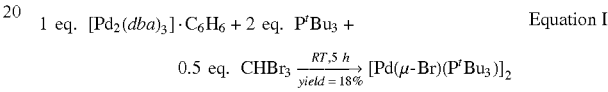

Equation I

Herein, the abbreviation "dba" stands for dibenzylidene acetone.

This first pathway provides only small yields (maximum 18%) for the desired Pd(I)-dimer and therefore is not suitable for producing higher amounts of the product.

In a second pathway, the known synthesis method additionally uses a Pd-COD compound besides the Pd-dba complex as source for Pd (ref to equation II):

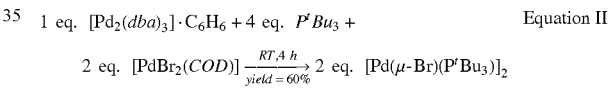

Equation II

The abbreviation "COD" stands for 1,5-cyclooctadiene, a cyclic diene compound. This second pathway provides higher yields (up to 60%) but at the same time additionally requires the use of the expensive starting material $[PdBr_2(COD)]$ besides the Pd complex $[Pd_2(dba)_3] \cdot C_6H_6$.

WO2011/012889 describes a third pathway for preparation of the $[Pd(\mu\text{-Br})(P^tBu_3)]_2$-complex using a mixture of $PdBr_2$ (diolefin) and $P^tBu_3$ in a solvent in presence of an alkali hydroxide. This process has the advantage that it does not use any $[Pd_2(dba)_3] \cdot C_6H_6$ as starting material. Hence, crystallization of this educt during the synthesis is avoided, which again avoids impurities in the final product.

However, WO2011/012889 describes 1,5-cyclooctadiene (COD) besides 2,5-norbornadiene (NBD) as preferred diolefin species. $PdBr_2(COD)$ as well as $PdBr_2(NBD)$ are difficult to handle (for example, storage is only possible under inert gas atmosphere at low temperatures). The starting materials of the process disclosed in WO2011/012889 have to be produced from the corresponding chlorinated derivate by halogen substitution with potassium bromide. The high costs and considerable precious metal losses associated with this method are serious drawbacks in view of a large scale industrial application. As a further drawback, organic residues from the diolefin starting materials may be present, thus contaminating the product.

J. F. Hartwig et al. describe the autocatalytic oxidative addition of bromobenzene to $Pd(P^tBu_3)_2$, wherein the $[Pd(\mu\text{-Br})(P^tBu_3)]_2$-complex is formed in low yields up to 16% in a mixture with other Pd compounds such as (P$^t$Bu$_3$)Pd(Ph)Br and (P$^t$Bu$_3$)$_2$Pd(H)Br (J. F. Hartwig et al., *J. Am. Chem. Soc.*, 2008, 130, 5842-5843).

Thus it is one object of the present invention to provide an alternative process for the preparation of the [Pd(μ-Br)(P$^t$Bu$_3$)]$_2$-complex, which overcomes the drawbacks of the prior art methods described above.

The new method of preparation should run under mild conditions and should use easy-to-handle, readily available educts. Working under inert gas atmosphere should be avoided. Furthermore, the use of expensive educt compounds such as [PdBr$_2$(COD)] or [Pd$_2$(dba)$_3$].C$_6$H$_6$], should be avoided. Additionally, any impurities of the final product with educt compounds should not be present. Finally, the process should provide the [Pd(μ-Br)(P$^t$Bu$_3$)]$_2$-complex in high yields.

This object is achieved by the method of the present invention. It provides an simple method for the preparation of the [Pd(μ-Br)(P$^t$Bu$_3$)]$_2$-complex, which is based on the use of PdBr$_2$ as one reaction partner (educt I) and Pd(P$^t$Bu$_3$)$_2$ as second reaction partner (educt II). The method of the invention is cost-effective, as, in a preferred embodiment of the invention un-reacted PdBr$_2$ is removed and reused after the reaction.

Another object of the invention is to provide a novel process for isomerization of allyl esters employing the [Pd(μ-Br)(P$^t$Bu$_3$)]$_2$-complex as catalyst.

Synthesis of [Pd(μ-Br)(P$^t$Bu$_3$)]$_2$-Complex

The method for preparing [Pd(μ-Br)(P$^t$Bu$_3$)]$_2$ according to the present invention is straightforward, economic and cost-effective. The method is essentially based on a comproportionation reaction, in which a Pd(ll) compound (=PdBr$_2$) is reacting with a Pd(0) compound (=Pd(P$^t$Bu$_3$)$_2$) to yield the [Pd(μ-Br)(P$^t$Bu$_3$)]$_2$ compound having the Pd atoms in the formal oxidation state +1. The overall-reaction equation for the method of the present invention can be formulated as follows (equation III):

Equation III

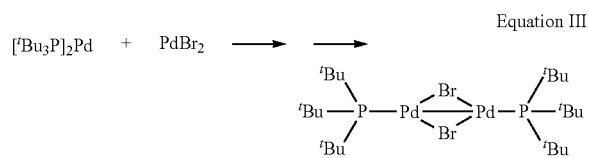

As can be seen from equation III, the only starting materials are PdBr$_2$ and Pd(P$^t$Bu$_3$)$_2$. The method according to the present invention does not make use of Pd sources comprising olefinic ligands such as dba or COD as previously described in the literature.

Pd(P$^t$Bu$_3$)$_2$ is commercially available from different vendors (e.g. Umicore AG & Co. KG, Hanau/Germany) or can be made according to well-known literature procedures. Thus the skilled person is well aware of how to obtain Pd(P$^t$Bu$_3$)$_2$.

Further, PdBr$_2$ is a commercially available Pd source. It is made from elemental Pd and a mixture consisting of hydrobromic acid (HBr) and bromine (Br$_2$). By such means a dark red to black-brown compound is formed (ref to K. Brodersen et al., *Z. Anorg. Allgem. Chem.* 1966, 348, 162-167).

The present invention provides a method for the preparation of the palladium complex of formula (I)

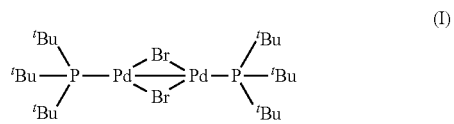

comprising the steps of
(a) preparing a mixture containing bis-(tri-tert.-butyl-phosphine)-palladium(0) (Pd(P$^t$Bu$_3$)$_2$) and palladium(II)-dibromide (PdBr$_2$) in an organic solvent and
(b) reacting the Pd compounds PdBr$_2$ and Pd(P$^t$Bu$_3$)$_2$ to form the Pd complex of formula (I).

In a further embodiment, the method additionally comprises the step (c) of removing un-reacted PdBr$_2$ from the reaction mixture.

In a further embodiment, the method additionally comprises the step (d) of removing the first and the second organic solvent to isolate the palladium complex of formula (I).

Generally the organic solvent is an aromatic hydrocarbon solvent from the group of benzene, toluene, the xylene isomers (o-, m- and p-xylene) and mixtures or combinations thereof. Additionally, aliphatic hydrocarbon solvents such as n-hexane, n-heptane, n-octane, cyclohexane or decaline as well as ether solvents such as anisol or methyl-tert.-butyl ether may be used. Mixtures of aromatic and aliphatic hydrocarbon solvents may also be used; aromatic hydrocarbon solvents are preferred. A particularly preferred solvent is toluene.

Generally, other solvents may be used, as long as the palladium complex of formula I is sufficiently soluble in the resulting solvent or solvent mixture and does not undergo decomposition, alteration or modification.

In a straightforward version of the method of the present invention, one of the Pd starting materials (either PdBr$_2$ or Pd(P$^t$Bu$_3$)$_2$) is weighed out and charged in the reaction vessel in solid form. The other Pd component is added thereafter, dissolved in a solution with the organic solvent. Preferably in this version, PdBr$_2$ is charged first in the reaction vessel and the phosphine complex Pd(P$^t$Bu$_3$)$_2$ is added in solution (i.e. in dissolved form). In a very simple version of the method of the present invention, the steps (a) and (b) may be combined and be conducted in one single step.

In a preferred version of the method of the present invention, the step (a) comprises the sub-steps of:
(a1) mixing of PdBr$_2$ in a first organic solvent,
(a2) mixing Pd(P$^t$Bu$_3$)$_2$ in a second organic solvent,
(a3) preparing a mixture containing PdBr$_2$ and the first organic solvent and Pd(P$^t$Bu$_3$)$_2$ and the second organic solvent.

Thereafter, the Pd compounds PdBr$_2$ and Pd(P$^t$Bu$_3$)$_2$ are reacted in step b) to form the palladium complex of formula (I).

In this preferred version, the first and/or second organic solvent may be an aromatic hydrocarbon solvent from the group of benzene, toluene, the xylene isomers (o-, m- and p-xylene) and mixtures or combinations thereof. Additionally, aliphatic hydrocarbon solvents such as n-hexane, n-heptane, n-octane, cyclohexane or decaline as well as ether solvents such as anisol or methyl-tert.-butyl ether may be used.

In the preferred version described above, the first and the second organic solvent employed in steps (a1) and (a2) are the same. A particularly preferred first and second solvent is toluene.

In step (a1) the starting material PdBr$_2$ is mixed with a first organic solvent. Depending on the type of solvent used, such mixture may result in a suspension or a complete solution.

Generally the concentration of $PdBr_2$ in the mixture/suspension/solution with the first organic solvent is in the range of about 0.01 to 0.5 mol/L, preferably in the range of 0.03 to 0.2 mol/L.

In step (a2) of the present method, $Pd(P^tBu_3)_2$ is mixed with a second organic solvent. Again, depending on the type of solvent used, such mixture may result in a suspension or a complete solution. Accordingly, the concentration of $Pd(P^tBu_3)_2$ in the mixture/suspension/solution with the second organic solvent should be in the range of about 0.01 to 1 mol/L, preferably in the range of 0.03 to 0.5 mol/L.

Generally, in step (a), a mixture containing $Pd(P^tBu_3)_2$ and $PdBr_2$ is prepared. Accordingly, in the preferred version of the method, in step (a3), a mixture of $Pd(P^tBu_3)_2$ and $PdBr_2$ in the first and the second organic solvent is prepared. In both steps, the molar ratio of $PdBr_2$ vs. $Pd(P^tBu_3)_2$ after mixing should be at least 0.8, preferably at least 0.9, and most preferred at least 1.0 (i.e. in stoichiometric amounts). Additionally, the molar ratio of $PdBr_2$ vs. $Pd(P^tBu_3)_2$ after mixing should not exceed a value of 1.4, preferably should not exceed a value of 1.2.

In step (b), the palladium starting compounds are reacted to form the palladium complex of formula I. The total concentration of Pd in the reaction mixture should be in the range of about 0.03 to 0.5 mol Pd/L; preferably in the range of about 0.05 to 0.2 mol Pd/L.

Stirring of the reaction mixture is carried out at temperatures in the range of 10° C. to 60° C., preferably in the range of 20 to 50° C. and particularly preferred at room temperature (herein defined as a temperature in the range of 20+/−2° C.).

The time-period for reacting the mixture in step (b) is in the range of 1 to 20 hours, preferably in the range of 1 to 16 hours.

In a further embodiment of the present invention, un-reacted $PdBr_2$ is removed from the reaction mixture after the reaction period. Typically, the un-reacted $PdBr_2$ is separated from the reaction mixture by filtration. The filtrated $PdBr_2$ is washed with an appropriate solvent, preferably with the organic solvent used in the reaction mixture, and hence re-used in a further synthesis. By that measure, the expensive Pd-containing starting material can be recycled for a further production run.

Generally, the removal of the organic solvents is done by solvent evaporation in vacuo, i.e. at low pressures and/or elevated temperatures. Typically, low pressures of <100 mbar are applied.

After removing of the solvents the desired Pd complex is obtained as a dark green solid substance. The separated Pd complex may be additionally washed with suitable further solvents, such as low boiling alcohol and/or ketone solvents and then dried. Drying may be performed by standard methods, for example at temperatures in the range of about 20 to 50° C. under vacuum for several hours.

Activation of $PdBr_2$

In general, commercially available $PdBr_2$ may be used as starting material for the method of the present invention. For example, $PdBr_2$ can be obtained from Umicore AG & Co. KG, Hanau/Germany (Prod. No. 68.2542.1340). As $PdBr_2$ is prone to a slow ageing process, in which it is converted to an insoluble, black crystalline modification, prolonged storage of the compound prior use should be avoided.

In a preferred embodiment of the invention, $PdBr_2$ is treated by an activation process before use as starting material for the method of the present invention. For this activation, a similar procedure is used as it is developed and reported by Gooßen et al for the activation of $RuCl_3 \cdot 3H_2O$ (see: L. J. Gooßen et al., *Adv. Synth. Catal.* 2008, 350, 2701-2707.) Following the procedure described therein, the activation process generally comprises a treatment of the substance in a solvent, preferably in a ketone solvent and particularly preferred in acetone.

Such activation process may be a dispersing process. In this case, large and insoluble $PdBr_2$ crystals are transformed into small, reactive $PdBr_2$ particles with chain structures. Such particles possess an enlarged surface area. In general, the activation is carried out for a time-period of at least 1 hour, preferably for least 5 hours at room temperature (=20+/−2° C.). The activation process may also be performed at higher temperatures in the range of 20 to 60° C., thus shortening the activation time.

Re-Use of Unreacted $PdBr_2$

A characteristic feature of the method of the present invention is the high degree of conversion of the Pd starting compounds to the desired reaction product. Recycling of the remaining un-reacted Pd compounds, in particular of $PdBr_2$, after product formation renders the method of the present invention highly economic. While the product is soluble in a mixture of the organic solvent(s) employed, remaining $PdBr_2$ can be separated from the solution of the product and re-used. According to the invention, the residual un-reacted $PdBr_2$ is washed with a further suitable organic solvent before being used again for another production run.

In a preferred embodiment, the first organic solvent and the second organic solvent are toluene and $PdBr_2$ is separated and finally washed with toluene.

Finally, the method of the present invention is simple, straightforward and applicable to an industrial, large scale production of the dimeric Pd-catalyst $[Pd(\mu\text{-}Br)(P^tBu_3)]_2$.

Process for Isomerization of Allyl Esters with $[Pd(\mu\text{-}Br)(P^tBu_3)]_2$

A further object of the invention is to provide a novel process for isomerization of allyl esters employing the $[Pd(\mu\text{-}Br)(P^tBu_3)]_2$-complex as a catalyst. In such isomerization reactions, enol esters are prepared. Enol esters are highly versatile key intermediates in organic syntheses such as asymmetric hydrogenations and polymerization reactions.

The term "allyl ester" used herein after refers to substituted and unsubstituted ally esters of the general type $R_1$—C(O)—O—$CH(R_2)$—$C(R_3)$=$CH_2$. In a preferred embodiment, the invention refers to a process for the isomerization of allyl esters of aromatic carboxylic acids such as benzoic acid allyl esters.

Compared to the traditional waste intensive multi-step methods, the precious metal catalyzed isomerization of allyl esters represents an atom-economical and environmentally friendly alternative, since the allyl esters are accessible in a broad structural diversity from easily available carboxylic acids and allylic alcohols.

Generally, the isomerization of allyl esters is associated with various problems such as side reactions and low yields.

Only few examples of a successful isomerization of allyl esters are known, using high amounts of iron or ruthenium catalyst (ref to Iranpoor et al., *J. Organomet. Chem.*, 1992, 423, 399-404 and Krompiec et al. *J. Mol. Cat. A: Chemical*, 2006, 253, 132-146).

It was found by the present inventors that the $[Pd(\mu\text{-}Br)(P^tBu_3)]_2$-complex can be used as a powerful catalyst for the isomerization of various carboxylic acid allyl esters of the following formula (II):

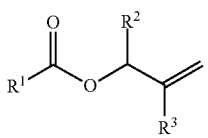

formula II

In formula II, the substituent $R_1$ represents a methyl, ethyl, $C_3$-$C_{15}$ alkyl, phenyl, alkyl-substituted phenyl, alkoxy-substituted phenyl, halogen-substituted phenyl, thiophenyl, $C_5$-$C_{10}$-aryl, or $C_4$-$C_{10}$-heteroaryl group, and the substituents $R_2$ and $R_3$ are independently selected from hydrogen, methyl, ethyl, $C_3$-$C_{10}$ alkyl groups or $C_5$-$C_{10}$-aryl groups.

Preferably, the substituent $R_1$ represents a $C_3$-$C_{15}$ alkyl, phenyl, alkyl-substituted phenyl or $C_4$-$C_{10}$-heteroaryl group, and the substituents $R_2$ and $R_3$ are independently selected from hydrogen, methyl, ethyl or $C_3$-$C_{10}$ alkyl groups.

In a particularly preferred embodiment, the substituent $R_1$ represents a $C_3$-$C_{15}$ alkyl, phenyl, o-, m- or p-tolyl, thiophenyl, furyl, pyridyl or pyrryl group, and the substituents $R_2$ and $R_3$ are independently selected from hydrogen, methyl, ethyl or $C_3$-$C_{10}$ alkyl groups.

Generally, the isomerization reaction of carboxylic acid allyl esters in the presence of catalytic amounts of [Pd(μ-Br)(P$^t$Bu$_3$)]$_2$-complex can be depicted by the following reaction (equation IV):

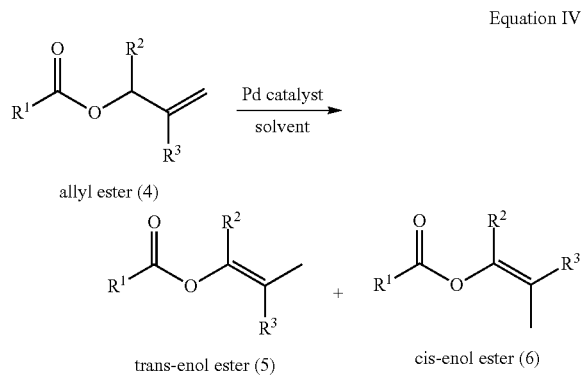

Equation IV allyl ester (4)    trans-enol ester (5)    cis-enol ester (6)

In equation IV, substance 4 denotes the allyl ester substrate, substance 5 denotes the trans-isomer and substance 6 denotes the cis-isomer of the resulting enol ester.

As an example, the results of the isomerization reaction of benzoyl allyl ester ($R_1$=phenyl, $R_2$=$R_3$=hydrogen) are shown in Table 1 in comparison to data from the literature.

As can be seen, the Pd(dba)$_2$ based method reported by Skrydstrup et al. *J. Am. Chem. Soc.* 2010, 132, 7998-8009 (entry 1) and the Ru based method reported by Krompiec et al. (cited above; entry 2) lead to the formation of the corresponding enol esters (5) and (6) in low yields not exceeding the value of 22% (ref to entry 1). In entries 1 and 2, the catalyst concentration is 0.5 mol-%, the reaction time is 3 hours.

In comparison, the Pd-catalyst [Pd(μ-Br)(P$^t$Bu$_3$)]$_2$ allows a nearly complete conversion of allyl benzoate into enol esters 5 and 6 already under mild conditions (50° C.), even in cases where very low amounts of the Pd-catalyst are employed (ref to entry 3 and 4).

In these experiments, the catalyst concentration is 0.25 mol-%, the reaction time is 3 hours (entry 3) and 2 hours (entry 4). A reduction of the process time to 2 hours shows nearly identical results. The enol ester products generally have a (E/Z)-selectivity of 1:2. The isomerization reactions occur nearly quantitative, only 1% of substance 4 is remaining in the product mixture.

Typical reaction times for the isomerization reaction are in the range of 0.5 to 16 hours, preferably 1 to 5 hours. Typical reaction temperatures are in the range of 20 to 120° C., preferably in the range of 20 to 100° C.

Suitable solvents are organic solvents such as aromatic or aliphatic hydrocarbons, ethers, esters or ketone solvents or mixtures thereof. Preferred solvents are aromatic hydrocarbons selected from the group of benzene, toluene, mesitylene and the xylene isomers (o-, m- and p-xylene) and mixtures or combinations thereof.

However, aprotic polar or nonpolar solvents such as THF, diglyme, diethyl ether or aliphatic solvents such as n-hexane are also suitable. In these experiments, the reaction time is 2 hours, only for entry 6, it is 40 min. For these solvents, the (E/Z)-selectivity of 1:2.2 is found for a total yield of 94-98% (entry 4-8).

Further examples underlining the broad application spectrum of the isomerization reaction of the present invention are described in the experimental section, particularly in Examples 7-11. Herein, the isomerization reactions of various substrates, such as a furyl allyl ester, a substituted allyl benzoate and allyl decanoate using the Pd-catalyst [Pd(μ-Br)(P$^t$Bu$_3$)]$_2$ are described in detail.

As demonstrated by the results of Table 1, the palladium complex [Pd(μ-Br)(P$^t$Bu$_3$)]$_2$ is a superior catalyst for the isomerization of a broad variety of allyl esters.

Under the present reaction conditions, commonly used functional groups are tolerated and allyl esters of aromatic, aliphatic and heterocyclic carboxylic acids are converted in high yield. These products serve as substrates in asymmetric hydrogenation and chiral ester with high ee are obtained.

TABLE 1

Results of the isomerization reaction of allyl benzoate with the different catalyst systems

| Entry | Pd-Source | Solvent | 4 [%] | 5 [%] | 6 [%] |
|---|---|---|---|---|---|
| 1 | [Pd(dba)$_2$] + P$^t$Bu$_3$,$^i$PrCOCl ligand | toluene | 72 | 10 | 12 |
| 2 | [RuClH(CO)(PPh$_3$)$_3$] | toluene | 88 | 0 | 5 |
| 3 | [Pd(μ-Br)(P$^t$Bu$_3$)]$_2$ | toluene | 1 | 26 | 63 |
| 4 | [Pd(μ-Br)(P$^t$Bu$_3$)]$_2$ | toluene | 1 | 30 | 65 |
| 5 | [Pd(μ-Br)(P$^t$Bu$_3$)]$_2$ | THF | 1 | 29 | 65 |
| 6 | [Pd(μ-Br)(P$^t$Bu$_3$)]$_2$ | diglyme | 1 | 30 | 52 |
| 7 | [Pd(μ-Br)(P$^t$Bu$_3$)]$_2$ | diethyl ether | 1 | 31 | 67 |
| 8 | [Pd(μ-Br)(P$^t$Bu$_3$)]$_2$ | n-hexane | 1 | 30 | 66 |

The following examples will further illustrate the invention without limiting the scope of the invention.

EXAMPLES

General Remarks: All operations are conducted under inert gas atmosphere (argon, nitrogen). All solvents used should be dry and free of oxygen.

All employed allyl esters are synthesized via esterification of the corresponding carboxylic acid and the corresponding alcohol following procedures described in the literature.

Example 1

Preparation of PdBr$_2$

PdBr$_2$ is readily available and can be prepared by the reaction of elemental Pd powder and a mixture of bromine (Br$_2$)

and bromohydrogen acid (HBr) according to the literature. The product is commercially available from Umicore AG & Co KG, Hanau/Germany (Prod. No. 68.2542.1340). As PdBr$_2$ undergoes a continuous ageing process, in which it is converted to an insoluble, black crystalline modification, prolonged storage of the compound should be avoided.

Example 2

Preparation of Activated PdBr$_2$

For the preparation of activated PdBr$_2$, a similar procedure is used as it was developed and reported for the activation of RuCl$_3$.3H$_2$O (ref to Gooβen et al., *Adv. Synth. Catal.* 2008, 350, 2701-2707). Accordingly, 3.99 g PdBr$_2$ (15.0 mmol) are stirred for 12 hours in 100 ml of acetone at room temperature (20° C.). Alternatively, stirring can be conducted for 4 hours at a temperature of 40° C. After removal of acetone in vacuo, a brownish compound is obtained.

Example 3

Synthesis of [Pd(μ-Br)(P$^t$Bu$_3$)]$_2$ 3.99 g of PdBr$_2$ (15.0 mmol; supplier Umicore AG & Co KG, Hanau, Germany) are suspended in 350 ml toluene by stirring. 7.66 g Pd(P$^t$Bu$_3$)$_2$ (15.0 mmol, supplier Umicore AG & Co KG, Hanau/Germany; Prod. No. 68.1844.5221) are dissolved in 150 ml toluene. The deep red solution is added to the PdBr$_2$/toluene suspension. The mixture turns into a green colour, thus indicating the formation of the Pd(I) species. The mixture is stirred for 16 hours at room temperature (20° C.). After that, the remaining unreacted PdBr$_2$ is removed by filtration. PdBr$_2$ is washed with additional 150 ml of toluene. The solvents are then combined and removed in vacuo (pressure<100 mbar). As a result, 8.1 g (10.5 mmol) of a dark green solid product are obtained, which corresponds to a yield of 70%.

Example 4

Synthesis of [Pd(μ-Br)(P$^t$Bu$_3$)]$_2$ Using Activated PdBr$_2$ 3.99 g of PdBr$_2$ (15.0 mmol; supplier Umicore AG & Co KG, Hanau, Germany; activated as described in Example 1) are suspended in 350 ml toluene by stirring. 7.66 g [Pd(P$^t$Bu$_3$)$_2$] (15.0 mmol, Umicore AG & Co KG, Hanau/Germany; Prod. No. 68.1844.5221) are dissolved in 150 ml toluene. The solution is added to the PdBr$_2$/toluene suspension. Immediately after starting the addition, the mixture turns into a green colour, thus indicating the formation of the Pd(I) species. The mixture is stirred for 16 hours at room temperature (20° C.). After that, the remaining un-reacted PdBr$_2$ is removed by filtration. PdBr$_2$ is washed with additional 150 ml of toluene. The solvents are then removed by evaporation (pressures <100 mbar). Finally, 10.1 g (13.0 mmol) of the dark green substance are obtained, which corresponds to a yield of 87%.

Example 5

Synthesis of [Pd(μ-Br)(P$^t$Bu$_3$)]$_2$ Using Partly Un-Reacted PdBr$_2$ 4.0 g of PdBr$_2$ (15.0 mmol, composed of a mixture of 3.0 g PdBr$_2$ (activated as described in Example 1) and 1.0 g PdBr$_2$ (un-reacted material from previous reactions), are suspended in 350 ml toluene by stirring. In parallel, 7.66 g [Pd(P$^t$Bu$_3$)$_2$] (15.0 mmol, Umicore AG & Co KG, Hanau/Germany; Prod. No. 68.1844.5221) are dissolved in 150 ml toluene. The solution is added to the PdBr$_2$/toluene suspension. The mixture is stirred for 16 hours at room temperature (20° C.). After that, the remaining un-reacted PdBr$_2$ is removed by filtration. PdBr$_2$ is washed with additional 150 ml of toluene. The combined solvents are then removed by evaporation (pressure <100 mbar). As a result, 9.5 g (12.2 mmol) of the dark-green substance are obtained, which corresponds to a yield of 82%.

Product Analysis:

Analysis of the products obtained in Examples 3, 4 and 5 are done by means of $^{31}$P-NMR and $^1$H-NMR methods. As described in the literature, the $^{31}$P-NMR spectrum shows a single signal at 86.4 ppm and the $^1$H-NMR spectrum shows a signal at 1.26-1.36 ppm for the products prepared according to the method of the present invention. Hence, the process of the present invention provides the [Pd(μ-Br)(P$^t$Bu$_3$)]$_2$-complex in high yields in the range of 70 to 90%.

Example 6

Isomerization of Allyl Esters (General Procedure)

A defined amount (5.0 or 2.5 μmol) of the catalyst complex to be tested (i.e. [Pd(dba)$_2$]+ligand P$^t$Bu$_3$+iPrCOCl; RuClH(CO)(PPh$_3$)$_3$ or [Pd(μ-Br)(P$^t$Bu$_3$)]$_2$) is placed in a reaction vessel. A 20 mm magnetic stirring bar is added. The reaction vessel is air tightly closed with a septal cap and is evacuated and flushed with nitrogen three times. In the next step, 2.0 ml of dry toluene and 50 μl of n-dodecane are added as internal standard by injection. The resulting mixture is stirred for a few minutes at room temperature (20° C.).

The allyl ester compound (1.0 mmol, substance 4) is added and the mixture is further stirred for additional 2 or 3 hours at a temperature of 50° C. After cooling, the reaction vessel is carefully opened and the reaction mixture is diluted with 2 ml ethyl acetate. Samples with a volume of 0.25 ml are taken by using a graduated pipette and are diluted in 2.0 ml ethyl acetate, washed with 2n aqueous NaCl solution (Brine), filtered over MgSO$_4$, and analyzed via gas chromatography (GC).

As demonstrated by the results of Table 1, palladium(I) tri-tert.-butylphosphine bromide dimer [Pd(β-Br)(P$^t$Bu$_3$)]$_2$ is a superior catalyst for the isomerization of allyl esters.

Example 7

Isomerization of Allyl Benzoate

The reaction is conducted as described in Example 6. Benzoic allyl ester of the following formula is reacted:

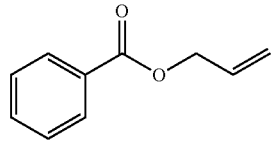

Degassed toluene (1.5 mL), the allyl benzoate (162 mg, 1.00 mmol) and a stock solution of [Pd(μ-Br)(P$^t$Bu$_3$)]$_2$ in toluene (0.5 mL, 2.5 μmol) are added to an oven-dried, nitrogen-flushed 20 mL vessel. The resulting mixture is stirred at 50° C. for 16 h. Once the reaction time is completed, the crude mixture is diluted with H$_2$O (10 mL) and extracted with diethyl ether (3×10 mL). The combined organic layers are washed with brine (2n aqueous NaCl solution, 10 mL), dried over MgSO$_4$, filtered and the volatiles are removed in vacuo to afford the corresponding enol ester, which is further purified by column chromatography (SiO$_2$, diethyl ether/n-pentane gradient). Prop-1-enyl benzoate is obtained as colorless liquid in a yield of 90% (146 mg) with an (E/Z)-selectivity of 1:2.

Example 8

Isomerization of Furoyl Allyl Ester

1-Furyl-3-carboxylic acid allyl ester of the following formula is reacted:

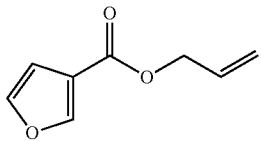

The reaction is conducted as described in Example 6. Degassed toluene (1.5 mL), the allyl furan-3-carboxylate (152 mg, 1.00 mmol) and a stock solution of [Pd(μ-Br)(P$^t$Bu$_3$)]$_2$ in toluene (0.5 mL, 2.5 μmol) are added to an oven-dried, nitrogen-flushed 20 mL vessel. The resulting mixture is stirred at 50° C. for 16 h. Once the reaction time is completed, the crude mixture is diluted with H$_2$O (10 mL) and extracted with diethyl ether (3×10 mL). The combined organic layers are washed with brine (10 mL), dried over MgSO$_4$, filtered and the volatiles are removed in vacuo to afford the corresponding enol ester, which is further purified by column chromatography (SiO$_2$, diethyl ether/n-pentane gradient). Prop-1-enyl furan-3-carboxylate is obtained as colorless liquid in a yield of 76% (115 mg) with an E/Z selectivity of 1:2.

Example 9

Isomerization of Allyl Decanoate

Decanoic acid allyl ester of the following formula is reacted:

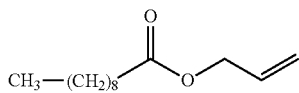

The reaction is conducted as described in Example 6. Degassed toluene (1.5 mL), the allyl decanoate (212 mg, 1.00 mmol, and a stock solution of [Pd(μ-Br)(P$^t$Bu$_3$)]$_2$ in toluene (0.5 mL, 2.5 μmol) is added to an oven-dried, nitrogen-flushed 20 mL vessel. The resulting mixture is stirred at 50° C. for 16 h. Once the reaction time is completed, the crude mixture is diluted with H$_2$O (10 mL) and extracted with diethyl ether (3×10 mL). The combined organic layers are washed with brine (10 mL), dried over MgSO$_4$, filtered and the volatiles are removed in vacuo to afford the corresponding enol ester, which is further purified by column chromatography (SiO$_2$, diethyl ether/n-pentane gradient). Prop-1-enyl decanoate is obtained as colorless liquid in a yield of 89% (189 mg) with an (E/Z)-selectivity of 1:2.

Example 10

Isomerization of but-3-en-2-yl Benzoate

The allyl ester of the following formula is reacted:

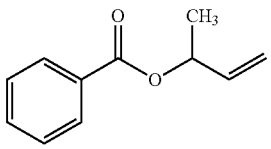

The reaction is conducted as described in Example 6. Degassed toluene (1.0 mL), the but-3-en-2-yl benzoate (176 mg, 1.00 mmol) and a stock solution of [Pd(μ-Br)(P$^t$Bu$_3$)]$_2$ in toluene (1.0 mL, 5.0 μmol) are added to an oven-dried, nitrogen-flushed 20 mL vessel. The resulting mixture is stirred at 50° C. for 16 h. Once the reaction time is completed, the crude mixture is diluted with H$_2$O (10 mL) and extracted with diethyl ether (3×10 mL). The combined organic layers are washed with brine (10 mL), dried over MgSO$_4$, filtered and the volatiles are removed in vacuo to afford the corresponding enol ester, which is further purified by column chromatography (SiO$_2$, diethyl ether/n-pentane gradient). But-2-en-2-yl benzoate is obtained as colorless liquid in a yield of 83% (146 mg) with an (E/Z)-selectivity of 1:3.

Example 11

Isomerization of 2-methallyl Benzoate

The benzoyl allyl ester of the following formula is reacted:

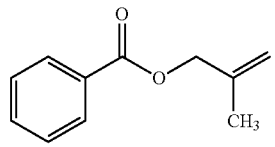

The reaction is conducted as described in Example 6. Degassed toluene (2.0 mL), the 2-methylallyl benzoate (176 mg, 1.00 mmol) and [Pd(μ-Br)(P$^t$Bu$_3$)]$_2$ (10 μmol) are added to an oven-dried, nitrogen-flushed 20 mL vessel. The resulting mixture is stirred at 50° C. for 16 h. Once the reaction time is completed, the crude mixture is diluted with H$_2$O (10 mL) and extracted with diethyl ether (3×10 mL). The combined organic layers are washed with brine (10 mL), dried over MgSO$_4$, filtered and the volatiles are removed in vacuo to afford the corresponding enol ester, which is further purified by column chromatography (SiO$_2$, diethyl ether/n-pentane gradient). 2-Methylprop-1-enyl benzoate is obtained as colorless liquid in a yield of 77% (136 mg).

The invention claimed is:
1. A method for the preparation of the complex of formula (I)

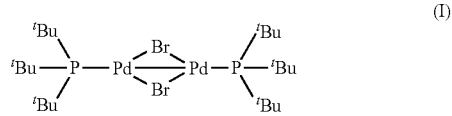

comprising the steps of
(a) preparing a mixture containing bis-(tris-tert.-butylphosphine)-palladium(0) (Pd(P$^t$Bu$_3$)$_2$) and palladium (II)-dibromide (PdBr$_2$) in an organic solvent and (b) reacting compounds PdBr$_2$ and Pd(P$^t$Bu$_3$)$_2$ to form the complex of formula (I), also designated as [Pd(μ-Br)(P$^t$Bu$_3$)]$_2$.

2. The method according to claim 1, wherein step (a) comprises the sub-steps:
(a1) mixing of PdBr$_2$ in a first organic solvent,
(a2) mixing Pd(P$^t$Bu$_3$)$_2$ in a second organic solvent,
(a3) preparing a mixture containing PdBr$_2$ and the first organic solvent and Pd(P$^t$Bu$_3$)$_2$ and the second organic solvent.

3. The method according to claim 1, further comprising the step (c) of removing un-reacted PdBr$_2$ from the reaction mixture.

4. The method according to claim 1, further comprising the step (d) of removing the organic solvent(s) to isolate the Pd complex of formula (I).

5. The method according to claim 1, wherein the organic solvent is an aromatic hydrocarbon solvent selected from the group of benzene, toluene, o-xylene, m-xylene, p-xylene, mesitylene or mixtures thereof.

6. The method according to claim 2, wherein the first and the second organic solvent are aromatic hydrocarbon solvents selected from the group of benzene, toluene, o-xylene, m-xylene, p-xylene, mesitylene or mixtures thereof.

7. The method according to claim 1, wherein the reaction time is in the range of 0.5 to 20 hours.

8. The method according to claim 1, wherein the reaction temperature is in the range of 10 to 60° C.

9. The method according to claim 3, wherein the un-reacted PdBr$_2$ is separated and re-used for the preparation of the complex of the formula (I).

10. The method according to claim 4, wherein removing of the first and the second organic solvent is made by solvent evaporation at low pressure.

11. The method according to claim 1, further comprising activating the PdBr$_2$ prior to use.

12. The method according to claim 11, wherein step of activating the PdBr$_2$ further comprises treating the PdBr$_2$ in an organic ketone solvent selected from the group of acetone, methylethylketone or diethylketone.

13. The method of claim 11, wherein the step of activating the PdBr$_2$ further comprises stirring the PdBr$_2$ in acetone.

14. A process for the isomerization of allyl esters of the formula II to enol esters,

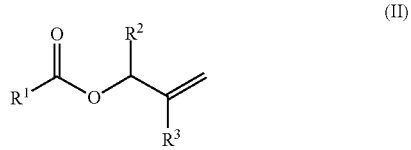

(II)

wherein
the substituent R$_1$ represents a methyl, ethyl, C$_3$-C$_{15}$-alkyl, alkyl-substituted phenyl, alkoxy-substituted phenyl, halogen-substituted phenyl, or C$_5$-C$_{10}$-aryl heteroaryl group,
the substituents R$_2$ and R$_3$ are independently selected from hydrogen, methyl, ethyl, C$_3$-C$_{10}$ alkyl or C$_5$-C$_{10}$-aryl groups,
which comprises using [Pd(μ-Br)(P$^t$Bu$_3$)]$_2$ as a catalyst.

15. The process according to claim 14, wherein the substituent R$_1$ represents a C$_3$-C$_{15}$-alkyl, phenyl, alkyl-substituted phenyl, or C$_4$-C$_{10}$-heteroaryl group, and the substituents R$_2$ and R$_3$ are independently selected from hydrogen, methyl or ethyl or C$_3$-C$_{10}$-alkyl groups.

16. The process according to claim 14, wherein the substituent R$_1$ represents a C$_3$-C$_{15}$-alkyl, phenyl, o-, m- or p-tolyl, furyl, pyridyl or pyrryl group, and the substituents R$_2$ and R$_3$ are independently selected from hydrogen, methyl, ethyl or C$_3$-C$_{10}$-alkyl groups.

17. The process according to claim 14, wherein the reaction time is in the range of 0.5 to 16 hours and the reaction temperature is in the range of 20 to 120° C.

18. The process according to claim 14, further comprising introducing organic solvents from the group of aromatic hydrocarbons or from the group of ethers into a reaction mixture with the catalyst.

19. The method of claim 6, wherein the first organic solvent and the second organic solvent are the same.

20. The method of claim 7, wherein the reaction time is in the range of 1 to 16 hours.

21. The process of claim 17, wherein the reaction time is in the range of 1 to 5 hours.

22. The process of claim 17, wherein the reaction temperature is in the range of 20 to 100° C.

23. A process for the isomerization of allyl esters of the formula II to enol esters,

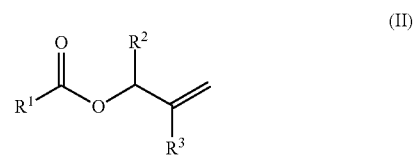

(II)

wherein
the substituent R$_1$ represents a methyl, ethyl, C$_3$-C$_{15}$-alkyl, phenyl, alkyl-substituted phenyl, alkoxy-substituted phenyl, halogen-substituted phenyl, or C$_4$-C$_{10}$-heteroaryl group,
the substituents R$_2$ and R$_3$ are independently selected from hydrogen, methyl, ethyl, C$_3$-C$_{10}$ alkyl or C$_5$-C$_{10}$-aryl groups,
which comprises using [Pd(μ-Br)(P$^t$Bu$_3$)]$_2$ as a catalyst.

24. The process of claim 14, wherein the substituent R$_1$ represents a phenyl group.

25. The process of claim 23, wherein the substituent R$_1$ represents a phenyl group.

* * * * *